(12) United States Patent
Bologurov et al.

(10) Patent No.: US 8,988,847 B2
(45) Date of Patent: Mar. 24, 2015

(54) METHOD AND APPARATUS FOR LOCAL MODIFICATION OF ATMOSPHERE

(75) Inventors: Sergey Bologurov, Kaluga Region (RU); Roman Rodkin, Moscow (RU)

(73) Assignees: Sergey Bologurov, Reglon (RU); Roman Rodkin, Moscow (RU); Phillipe Barnard, Châtelet (BE)

( * ) Notice: Subject to any disclaimer, the term of this patent is extended or adjusted under 35 U.S.C. 154(b) by 1194 days.

(21) Appl. No.: 12/937,175

(22) PCT Filed: Mar. 20, 2009

(86) PCT No.: PCT/IB2009/005049
§ 371 (c)(1),
(2), (4) Date: Nov. 17, 2010

(87) PCT Pub. No.: WO2009/125264
PCT Pub. Date: Oct. 15, 2009

(65) Prior Publication Data
US 2011/0049257 A1    Mar. 3, 2011

(30) Foreign Application Priority Data
Apr. 10, 2008  (RU) .................. 2008113605

(51) Int. Cl.
*H01T 23/00* (2006.01)
*A01G 15/00* (2006.01)
*A61N 1/44* (2006.01)

(52) U.S. Cl.
CPC .............. *A01G 15/00* (2013.01); *H01T 23/00* (2013.01); *A61N 1/44* (2013.01)
USPC ............................ 361/231; 361/230; 361/235

(58) Field of Classification Search
CPC ........................................................ H01T 23/00
USPC ........................................................ 361/231
See application file for complete search history.

(56) References Cited

U.S. PATENT DOCUMENTS

| | | | |
|---|---|---|---|
| 7,156,898 B2 * | 1/2007 | Jaisinghani | 95/63 |
| 2005/0051420 A1 * | 3/2005 | Botvinnik et al. | 204/164 |
| 2008/0314250 A1 * | 12/2008 | Cowie et al. | 96/86 |

FOREIGN PATENT DOCUMENTS

| | | |
|---|---|---|
| EP | 1652423 | 5/2006 |
| RU | 2090057 | 9/1997 |
| RU | 2161881 C2 | 1/2001 |
| RU | 2297758 | 4/2007 |

OTHER PUBLICATIONS

International Search Report for Application No. PCT/IB2009/005049 (3 pages).

* cited by examiner

*Primary Examiner* — Rexford Barnie
*Assistant Examiner* — Toan Vu
(74) *Attorney, Agent, or Firm* — Kevin R. Erdman; Brannon Sowers & Cracraft PC

(57) ABSTRACT

The invention concerns environmentally compatible methods and apparatuses for local modification of atmosphere, and in particular, for causing precipitation, dissipating fogs and/or clouds, removing air-pollutants in a target area. SUBSTANCE: the method involves applying air ionizers (1a, 1b, 1c) to generate ion flows into atmosphere to form convective flows and/or spatial charges. To control characteristics of the ion flow, it is proposed to use one or multiple air ionizers (1a, 1b, 1c) provided with variable-inclination electrode working cells. EFFECT: wide application of an air ionizer (1) with variable layout (inclination angle) of the electrodes in weather condition modification over a target area.

8 Claims, 7 Drawing Sheets

METHOD AND APPARATUS FOR LOCAL MODIFICATION OF ATMOSPHERE

CROSS-REFERENCE TO RELATED APPLICATION

This application is a National Stage filing of International Application Serial No. PCT/IB2009/005049, which claims the benefit of Russian Application Serial No. RU 2008113605, filed Apr. 10, 2008, the disclosures each of which are expressly incorporated herein by reference.

FIELD OF THE INVENTION

The invention relates to methods and apparatuses for controlling atmospheric conditions over a target area; the invention can be used for causing the precipitation of water or dissipating fog and/or clouds, as well for environmental means.

BACKGROUND OF THE INVENTION

Various techniques and apparatuses are known in the art for treating atmospheric conditions by electrical means. Introduction of electrical methods for weather control and modification instead of using chemical agents or fuel combustion has perfect ecological properties and offers very promising perspectives. Apparatuses called air ionizers induce or rearrange spatial charges and/or convective flows of ionized air in the atmosphere over a target earth surface area that results in changing the phase state of atmospheric water.

The most advanced atmospheric ionizers generate ion flow by producing a corona discharge in an electrical conductor. Early versions of such devices comprised separate conductors extended for a long distance over a ground surface. Said conductors had insignificant effect on the atmospheric formations because of incapability to induce focused ion flows and/or large spatial charges in the atmosphere. A series of improvements led to development of ionizers that had more compact sizes and were capable to generate directional ionized air flows and to cause more effective changes in the atmospheric conditions within a specified area. Weather modification methods can be used for solving different weather problems (artificial initiation of precipitation, dispersal of fog or mist, pumping up surface air etc.) and should take into account the changeable weather conditions and the behaviour of atmospheric processes. To solve various weather problems it is required to use air ionizers with capability of adjustment of the created ion flow parameters, e.g. density, directivity ratio, stability etc.

A typical ionizer comprises a ion generator supplied with, as a minimum, two electrodes: an ionizing electrode (electron emitter) generally consisting of an electrical conductor of a small cross-section, and a ground electrode, which can be executed in different versions. The conductors are mounted on a supporting frame in such a way that they are above a ground surface. The ionizer comprises a control unit to control a voltage potential on the electrodes. Advanced versions of ion generators include auxiliary electrodes, in particular, an extracting electrode consisting of an electrical conductor enabling continuous drain flow of electrons and ions from the ionizing electrode and causing persistent ion flow into the atmosphere.

The ionizer described in the Russian patent RU 2090057 is among the first successful apparatuses generating upward ion flow into the atmosphere. Said ionizer comprises working cells; each cell is supplied with an ionizing electrode and a ground electrode, positioned in its entirety in parallel planes within each one cell so that some cells are horizontal and others are vertical or tilted. The generator can also include an extractor, e.g. an electrostatic or another device. For more efficiency said generator can be supplied with an ion flow humidifier and/or air blower to further adjust ion flow rate and/or intensity. Directional properties of the ionized air flow depend on design features and mutual alignment of the electrodes. An alternative structure of said ion generator is shown in FIG. 3 of the document under consideration. Said design is a prototype for a number of follow-up developments.

Besides compact sizes and general efficiency in producing the directional ion flow, said generator has a braced structure with no capability of operational adjustment of the spatial position of working cells of said ionizer that is required for further controlling the characteristics of the produced ion flow.

The Russian patent RU 2297758 describes an ionizer that can contain an additional electrode-extractor besides an ionizing electrode and a ground electrode. Said ionizer has all three electrodes positioned in parallel planes and at equal distances from each other, just as in the patent RU 2090057, but differs from the latter in that its emitter is made in the form of a cube with the edges of a specified length. Said cube is composed of lateral faces placed vertically and a bottom face placed horizontally, and has no top face. As a subcase of the ionizer of the patent RU 2090057, the apparatus described in the patent RU 2297758 has the same disadvantage that is a braced structure. The disadvantage lies in the fact that the weather conditions resembling at first sight may be caused by various meteorological conditions (e.g. fogs can differ in source, height and density) and the purposes can differ (e.g. complete or partial fog dispersal, initiation or prevention of precipitation) while performance characteristics of said ionizer are very limited. The specified apparatuses allow changing the operating parameters by controlling voltage and current supplied to electrodes as well the selective use of auxiliary equipment, e.g. a steam generator, an air blower etc.

However, these measures are often ineffective and can not provide a full control of parameters of the created ionized air flow due to a variety of meteorological factors and a dynamic nature of atmospheric processes. The efforts to develop an ionizer being suitable for use in different conditions and being capable of operational adjustment of the created ion flow with a high efficiency without changing its configuration, have not achieved positive results.

DISCLOSURE OF THE INVENTION

The invention disclosed herein solves two problems: 1) controlling the created ionized air flow within a wide range of weather conditions and 2) developing the ionizer with a higher level of control of ionized air characteristics.

The first set problem is solved by that the specified method of local atmosphere modification includes controlling the generated ion flow over a target area by changing the inclination angle of working cells of one or multiple air ionizers.

The second set problem is solved by that the ionizer comprises three electrodes: a shielding electrode, an emitter and an extractor being placed in a parallel way; each electrode comprises coupled working cells formed by an electrical conductor that is arranged in a plane; all working cells of each electrode are tilted to the common center; each working cell of each electrode is mounted on a supporting frame in such a way that it is possible to adjust its inclination to an axis plane of the apparatus and to change its position relating to the other two opposite electrodes with their parallel orientation being unchanged; meanwhile the upper part of the extracting electrode and the upper part of the shielding electrode are located above the emitting electrode during operation.

Methods of local atmosphere modification by applying adjustable ion flow are known in the prior art, but all said methods propose to adjust the ion flow by changing the voltage on the ionizing electrode or applying the auxiliary equipment (see said patents for more information). However, the authors of the invention have not found in prior art the samples of controlling the created ion flow by operational changing the ionizer configuration (geometrical structure) and, in particular, by changing the inclination angle of its electrodes.

The prior art offers a number of ionizer configurations wherein the ionizing electrode or the ground electrode are supplied with tilted working cells. For example, the system for weather modification described in the patent RU 2161881 comprises the ionizing electrode (emitter) that is a frame arranged in the form of an equilateral pyramid with an electric conductor reeled on its edges. However, just compact sizes are found in the description of said technical solution among advantages relative to the art. The patent description contains no other information on alternative technical results concerning said execution of an ionizing electrode. Said invention does not offer to adjust parameters of the created ion flow by changing the configuration of the electrodes. Meanwhile, said ionizer configuration does not allow creating a highly directional and a perfectly concentrated ion flow under various meteorological conditions because a spatial position of its working cells serves more for creating the stable spatial charges than forming the convective air fluxes.

The Russian patent RU 2233578 describes an apparatus for creating a stable ascending ionized air flow that comprises at least one ionic generator further comprising an ionizing electrode and a ground electrode, placed in a parallel way around the third electrode-extractor, thus forming a tilted surface that becomes narrower towards the bottom part of said ion extractor. Said extractor is an electric conductor positioned along the axial line of a geometric body while the ionizing electrode is positioned on the side surface of said geometric body, i.e. the extractor is the 'umbrella handle' in relation to the figure formed by the ionizing electrode. Said design allows for the optimum utilization of the emitter surface and does not hinder the performance of its parts located at different heights thus providing an increase in the output of electrons emitted from the ionizing electrode and creating a directional ascending ionized air flow of high density in the atmosphere. The apparatus allows further adjustment of concentration of the created ion flow that is achieved with the use of an electromagnetic coupling device. However said ionizer serves generally for the only task of weather modification that is deranging anticyclonic circulation in the atmosphere that results in accumulation of clouds followed by precipitation. However a form of the emitter does not allow applying said apparatus for fog dispersal since it is intended for application in the sunny weather.

The method and the apparatus described herein serves for solving a lot of problems concerning the weather modification over a target earth surface area. Therefore it is difficult to select a technical decision in the prior art that is the most closely relates to the invention proposed.

The invention disclosed herein will be further illustrated with drawing figures.

DETAILED DESCRIPTION OF THE INVENTION

Figure 1:
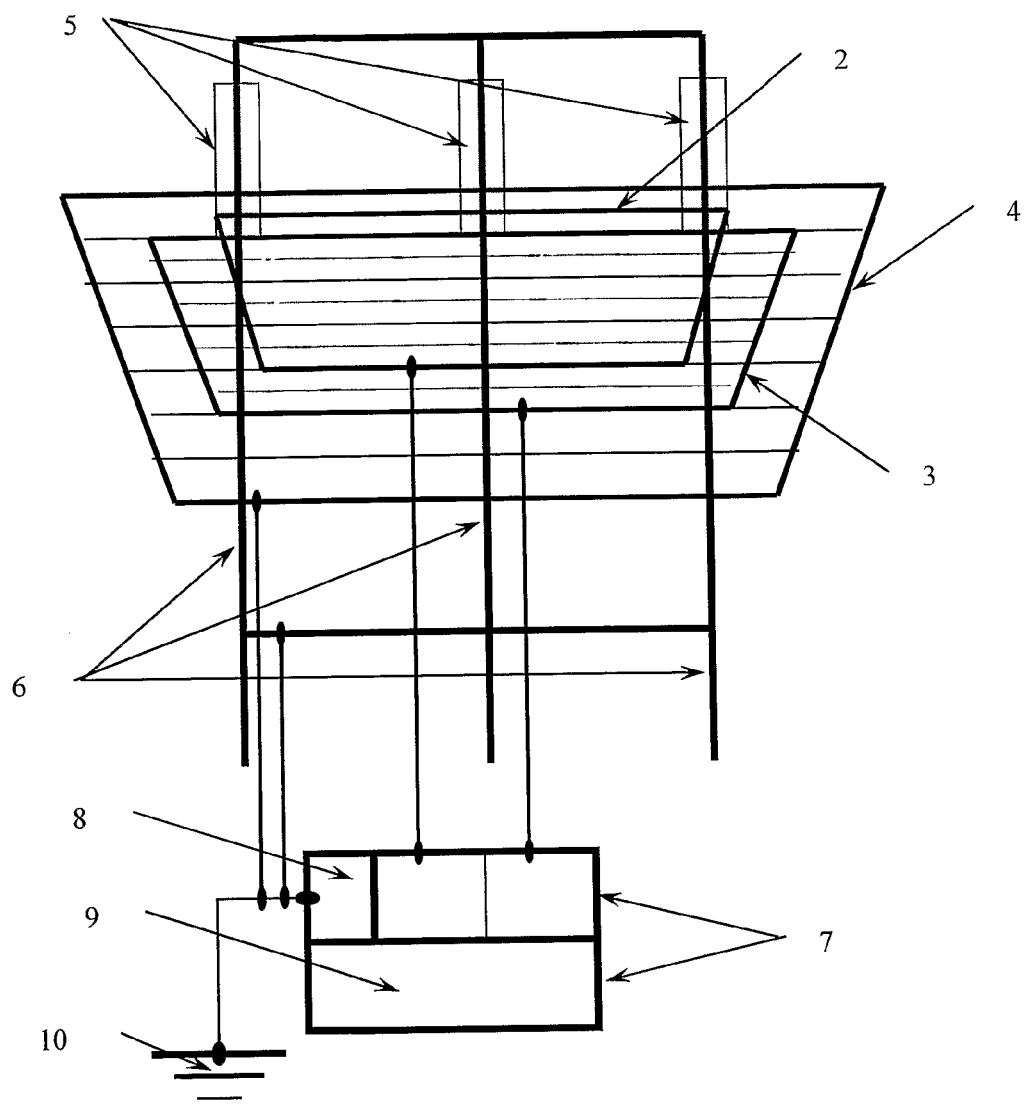
FIG. 1 is a side view of an ionizer.
Figure 2:
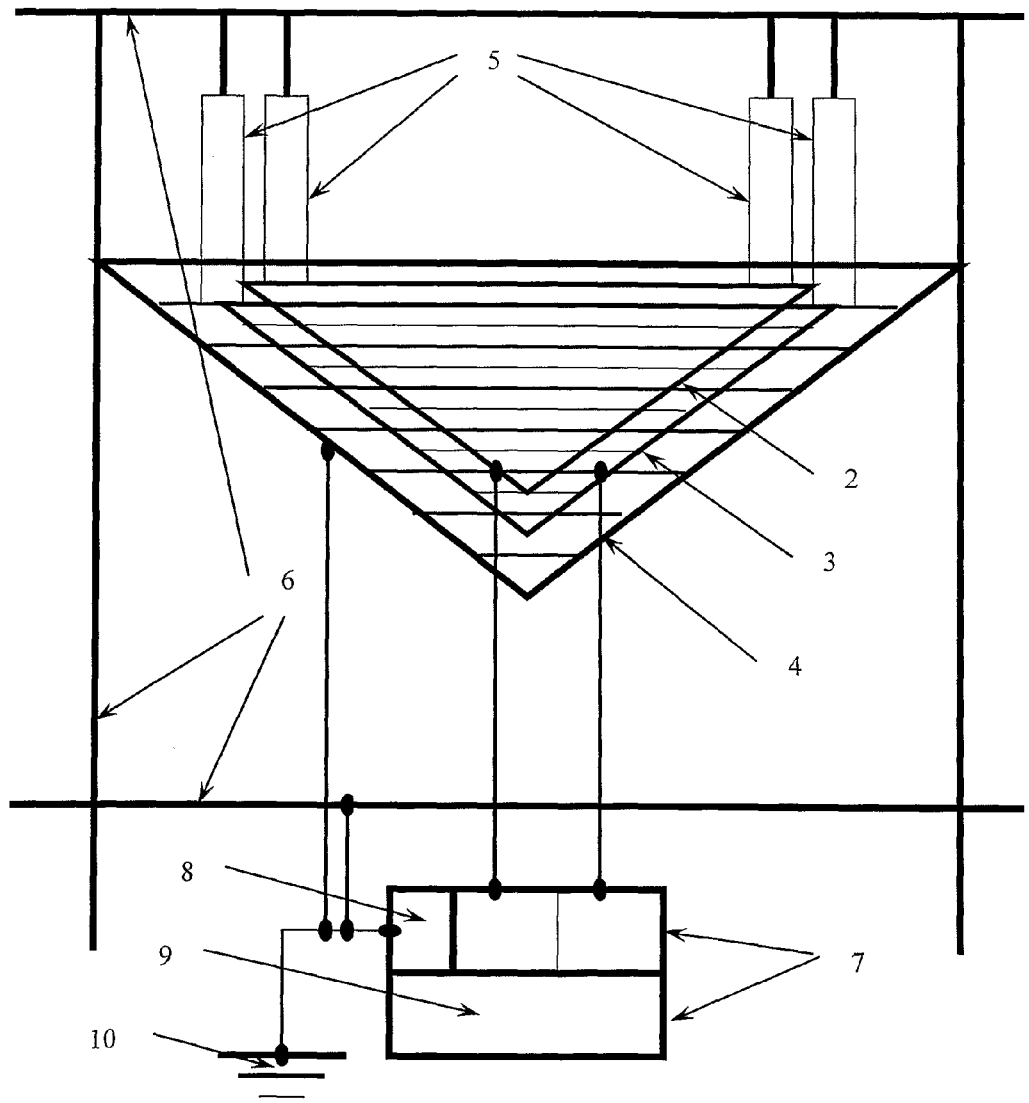
FIG. 2 is a face view of the ionizer.
Figure 3:
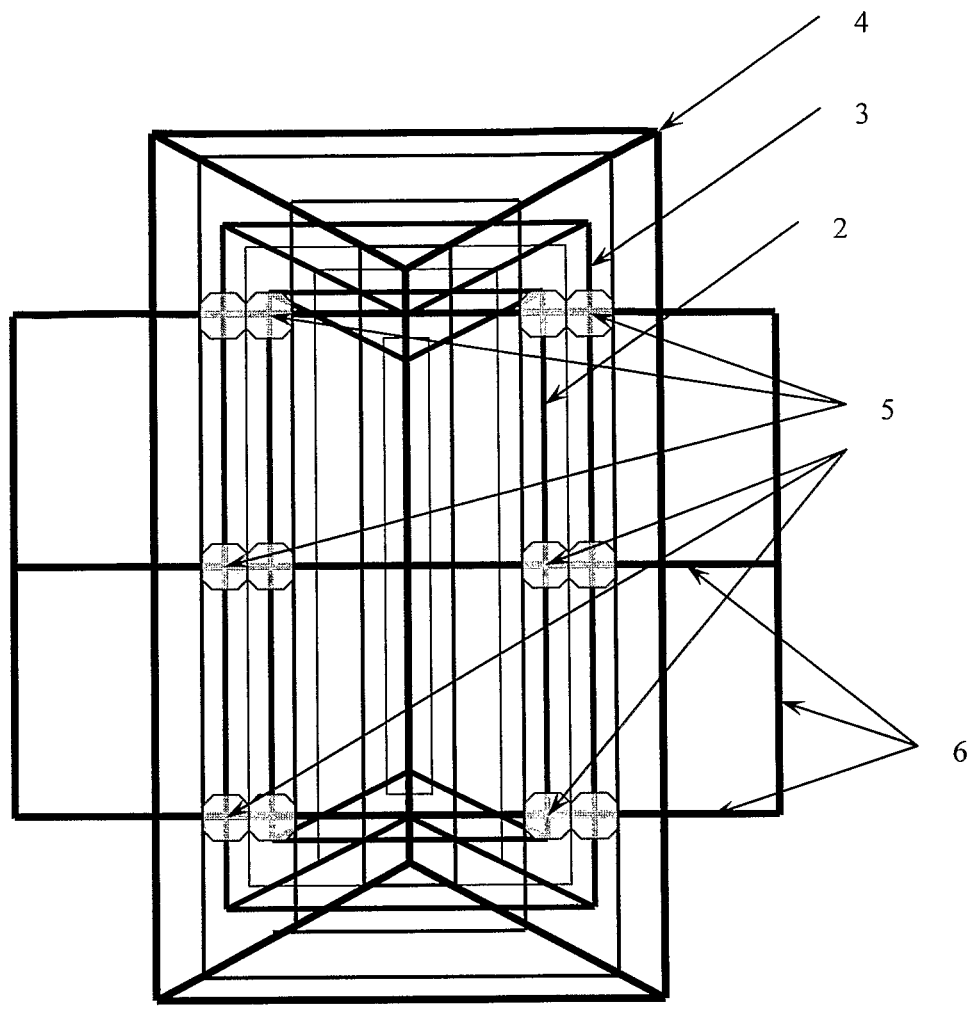
FIG. 3 is a top view of the ionizer.

The specified method of local atmosphere modification uses one or multiple apparatuses (ionizers) creating ionized air flows over a target earth surface area.

The ionizer 1 (1a, 1b, 1c) comprises three electrodes that are an extractor 2, an emitter 3 and a shielding electrode 4. The electrodes are mounted on a supporting frame consisting of orthogonal strength members 6 and are fitted with insulators 5. Before operation the ionizer is to be set in such a way that the strength members 6 are vertical or horizontal and the shielding electrode 4 is grounded and is placed beneath the emitter 3 while the extractor 2 is located above said emitter.

The emitter 3 is the main ionizing electrode comprising a number of coupled working cells that are tilted to the common center thus forming a side surface of an elongated pyramid or of a similar geometric body. Each emitter cell comprises an electric conductor arranged in one plane in its entirety. Said conductor has a small cross-section and hence a highly-curved surface. This results in maximizing the quantity of electrons escaping from the ionizing electrode. The diameter of the conductor is from 0.1 to 0.5 mm. The working cells of the emitter 3 are attached to the horizontal members of the main frame with the insulators 5. An attachment fitting (not shown) serves for connecting the working cells of the emitter 3 with the members 6 of the main frame and is intended to adjust the position of said cells in both vertical and horizontal planes providing a desired angle between the opposite cells (e.g. the inclination angle). For example, the attachment may be executed as pivot fittings joining together the bottom parts of the working cells as well any fittings fixing the upper parts of said cells on the horizontal members 6 of the frame.

During operation the shielding electrode 4 is placed beneath the emitter 3. The electrode 4 is attached to the vertical members 6 of the frame. Said electrode, as the electrode 3, can be moved up and down in a vertical plane as well in a horizontal plane in a parallel way with the emitter 3, thus increasing or decreasing the distance between surfaces of the electrodes 4 and 3 to supply a desired voltage on the emitter, that results in maximizing the performance of the apparatus at a given instant. The electrode 4 is made of a number of coupled working cells that are tilted to the common center in the same manner as the electrode 3 does. Each cell of the electrode 4 consists of a small section conductor arranged in its entirety in one plane along the emitter plane. The electrode conductor 4 is from 2 to 4 mm in diameter that is larger than a cross-section of the ionizing electrode 3. The upper part of the electrode 4 is located above the upper part of the electrode 3 even at the maximum distance from the electrode 3.

The extractor 2 is attached to the horizontal members 6 of the main frame with the insulators 5 that are used to adjust the position of the extractor in a parallel way with the electrodes 3 and 4. The extractor 2 is located above the emitter 3 and comprises a number of the working cells positioned in a parallel way with the working cells of the emitter 3 and the ground electrode 4. The conductor of said extractor is located in one plane in its entirety and has a small cross-section that is less than that of the electrode 4. For example, it can be from 0.3 to 0.7 mm in diameter. The outflow of electrons emitted by the emitter 3 is continuous due to a parallel position of the extractor 2 and said emitter 3 and has the maximum intensity as the upper part of said extractor is located above the upper part of said emitter even at the minimum distance between them.

Thus the upper parts of the emitter working cells are always recessed against the upper parts of the electrodes 2 and 4 thus maximizing the outflow of electrons from the electrode 3 and hence the density of a created ascending flow of ionized air.

The distance between the horizontal conductors of the emitter 3 within a working cell is from 10 to 60 mm. The same distances are between the horizontal conductors of the extractor 2 and the shielding electrode 4.

The apparatus described in the invention is from 2 to 10 meters in length and in width depending on application and other factors, e.g. a type of installation (stationary or portable).

The main operating potential is always negative and is supplied from a high-voltage power unit 7 to the emitter 3 that is an ionizing electrode. Depending on the task set, the ionizer size, the distances between the electrodes and the current meteorological conditions, the operating voltage can vary from 20 to 100 kW that corresponds to the current from 0.1 to 10 mA.

The extractor 2 can perform two functions: it is energized by the negative potential supplied from power unit or it serves as a transmitter sending data to an electronic device 8 that is a part of said power unit. When the electrode 2 is used as a sensor, it is not alive and just measures the values of voltage and current induced in said electrode by the high voltage supplied to the emitter 3 that is located in close vicinity to the electrode 2. The data are used for controlling the distance between the surfaces of the electrodes 2 and 3 so that the outflow of electrons from the emitter surface is at maximum.

The potential on the electrode 2 is actually negative whereas it is always positive comparing with that on the emitter. The electrode 2 is also called a secondary electrode/emitter because a potential induced on said electrode, depending on the potential supplied to the emitter 3, provides a continuous outflow of electrons from the extractor 3 that results in an increase of the ionizing feature of the apparatus and creating a stable ionized air flow.

To provide the efficient outflow of electrons from the ionizing electrode 3, the power unit 7 can comprise a stabilizing device 9 that serves for holding a desired level of high negative voltage at the emitter 3. Said stabilizing device is used to prevent the apparatus from a short-circuit failure that can occur under certain meteorological conditions due to closely spaced electrodes, for example, the emitter 3 and the shielding electrode 4. For safety reasons, the apparatus should be properly grounded by a grounding contact 10.

A high voltage supplied to the electrode 3 induces a corona discharge thus ionizing the surrounding air. It is followed by an increase in intensity of a created electric field that rises higher than the intensity of the Earth's electric field being equal 130 volt per meter approximately.

As a result of ionization, negatively charged ions and free electrons are formed. Passing through the extractor 2, they obtain an additional portion of kinetic energy and rise upwards into the atmosphere thus producing an ascending ionized air flow. The created negatively charged ions serve as condensation nuclei for water vapor in the atmosphere, e.g. they attract molecules of water vapor thus releasing heat energy and, hence, increasing the temperature of the surrounding air. Therefore, light-weight negative ions joined with water molecules continue moving upward. They receive an additional energy required for their upward movement from an electric field created by the ionizer. While the atmosphere air volume is heated and a vertical ionized flow is formed in the area above the upper part of the apparatus/ionizer, a pressure gradient exists in said area and the low atmospheric pressure region is filled with new portions of the surrounding air to reduce the pressure gradient to zero. The process repeats continuously thus maintaining a stable ionized air flow that moves vertically upward.

DESCRIPTION OF EMBODIMENTS OF THE INVENTION

1. The described method of artificial precipitation in clouds, that are not properly extended vertically and have insufficient water content, consists in the use of an air ionizer for producing a directional vertical flow of ionized air. Water molecules is attracted to negative ions within the flow, therefore water content of surrounding air increases and after a while it reaches the level required to initiate precipitation.

Figure 4:
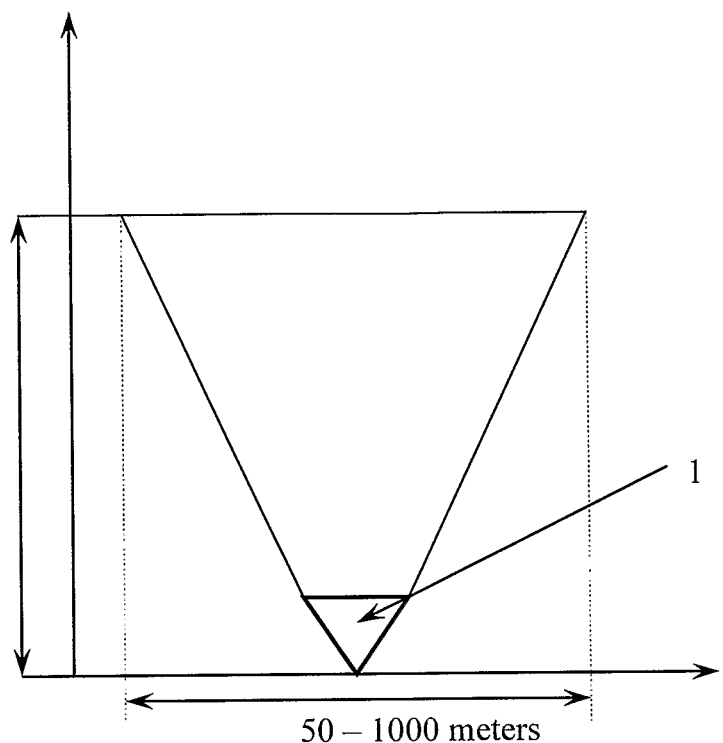
FIG. 4 illustrates the scale-adjusted scattering of an ionized flow depending on the height of a cloud base and on the angle between the opposite working cells of the ionizer electrodes.
Figure 5:
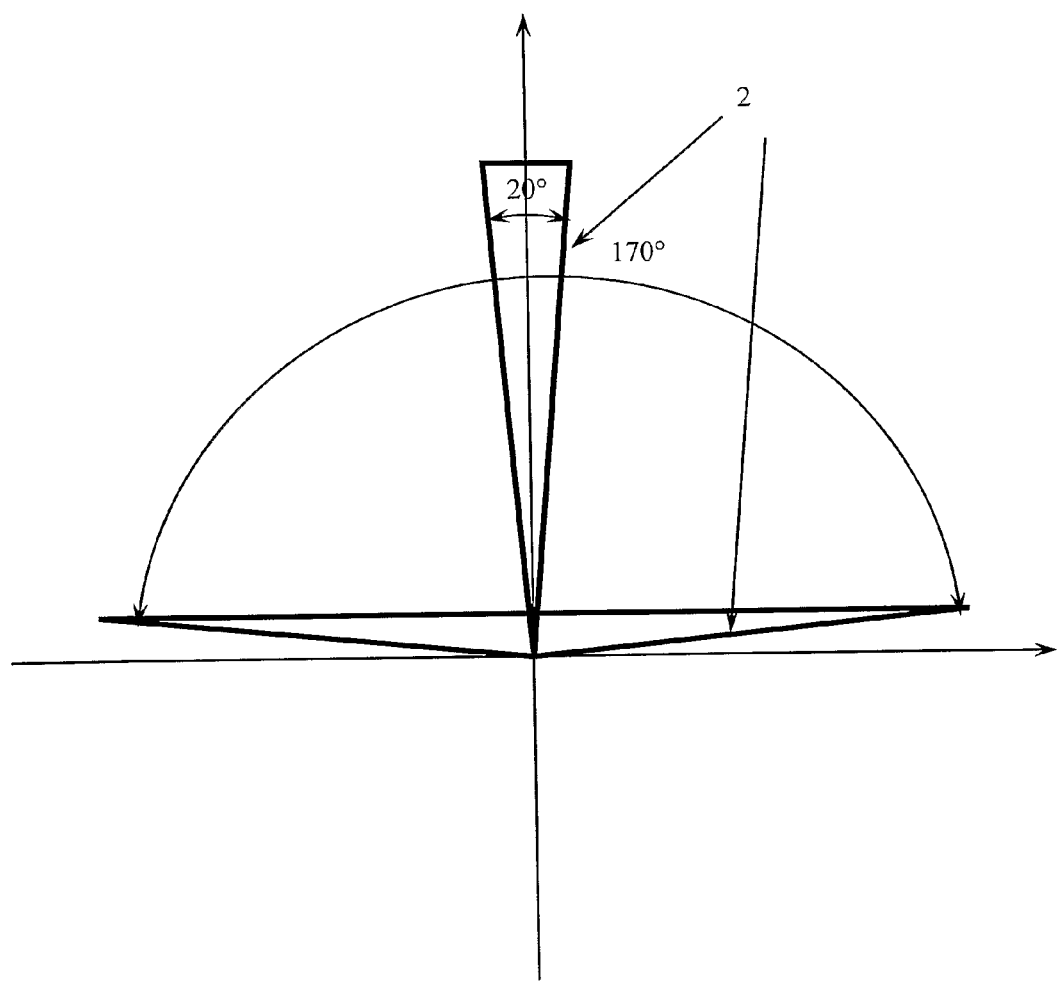
FIG. 5 illustrates the capability of adjusting the angle of inclination between the working cells by an example of the inner electrode (emitter).
Figure 6:
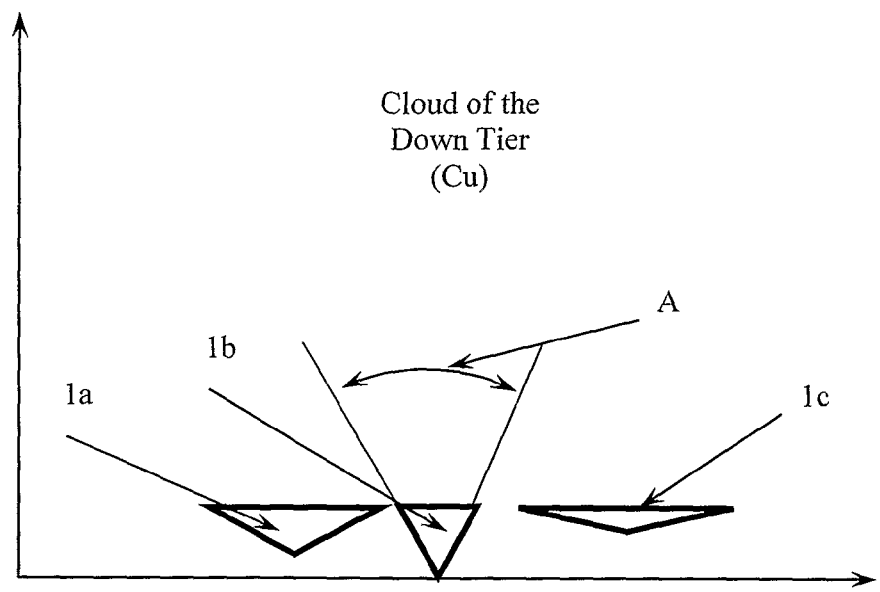
FIG. 6 illustrates three ionizers/apparatuses with different inclination angles between the side surfaces: 1a, 1b, 1c. The ionizers/apparatuses under 1a, 1b, 1c are located in the same place and a particular assembly is selected depending on the task set. In particular, the figure illustrates the ionizer assembly 1b selected for influencing the cloud formation in the lower layers of the atmosphere to increase the water content resulting in the precipitation. Letter 'A' herein specifies the treated area depending on the selected ionizer/apparatus.

FIG. 4 illustrates the scale-adjusted scattering of an ionized flow depending on the height of a cloud base and on the angle between the opposite working cells of the ionizer electrodes. For example, to stimulate vertical formation of heap clouds to cause precipitation in a local earth area, the ion flow should be directed to the center of the heap cloud, since naturally-occurring air flows move upwards within the cloud and the descending currents are created at its edges.

Figure 8:
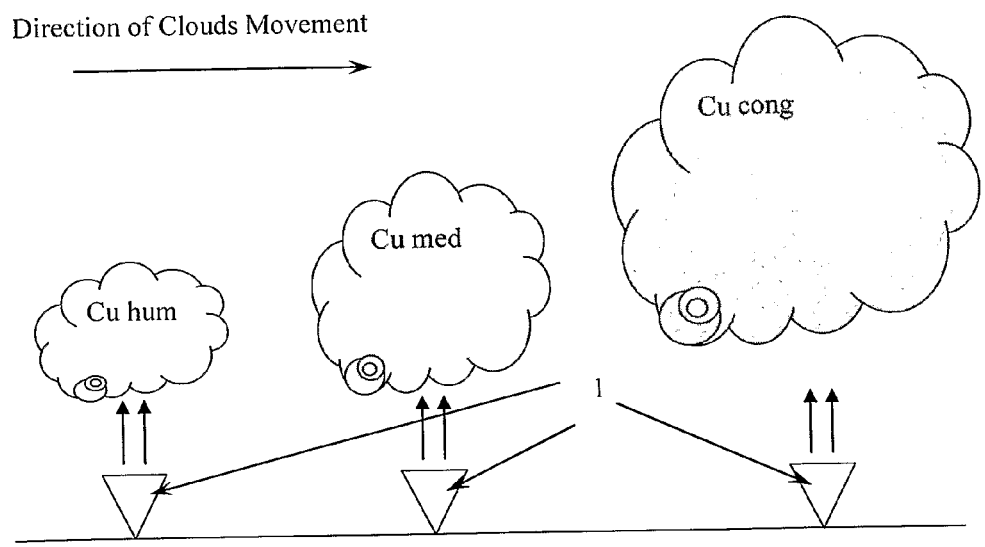
FIG. 8 illustrates the process of the heap cloud formation by an example of the step-by-step treatment of clouds. First the cumulus clouds of fine weather, called as 'Cumulus humilis' (Cu hum), are treated thus developing into Cumulus mediocris clouds (Cu med) that are further transformed into Cumulus congestus clouds (Cu cong) to become Cumulonimbus clouds being capable to produce precipitation. The upward arrows show the direction of an ionized air flow.

FIG. 8 illustrates an example of artificial precipitation in cumulus clouds of fine weather, called 'Cumulus humilis' (Cu hum). The treatment of the clouds causes them to develop into Cumulus mediocris clouds (Cu med) that are further transformed into Cumulus congestus clouds (Cu cong) being capable to produce rain due to high water content and greater vertical extent. If there is not enough water content in the surrounding air, it is necessary to spray fresh or salt water at maximum altitude above the ground and within the area of the working range of the apparatus/ionizer.

Figure 9:
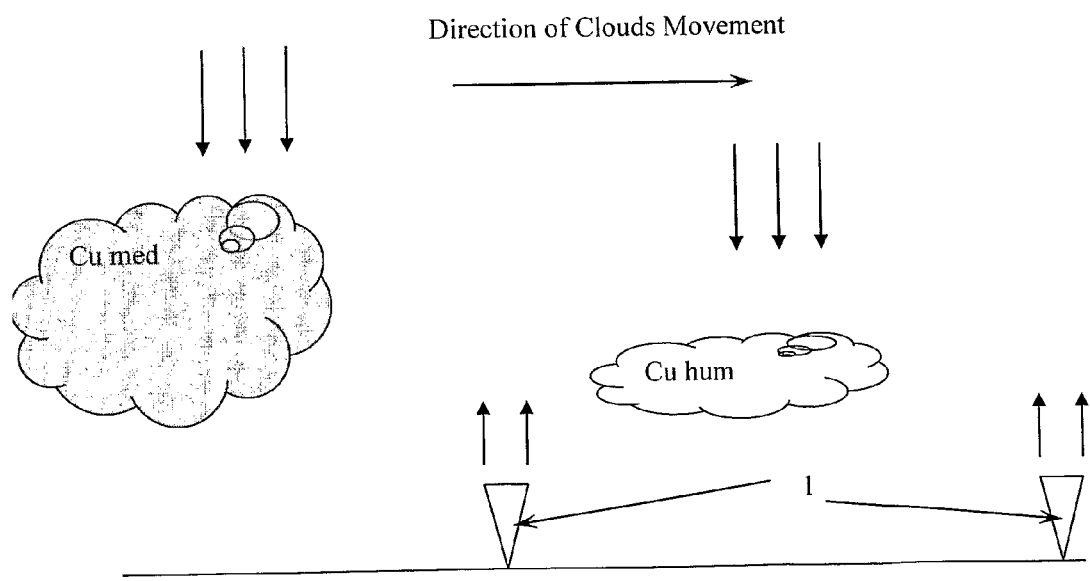
FIG. 9 shows an example of step-by-step cloud dispersion. The upward arrows show the direction of an ionized air flow, the downward arrows show descending warm and dry air flows causing the dispersion of the clouds.

2. Cloud dispersal is achieved by treating the clouds with countervailing downflows of dry and warm air that are caused by creating an ascending ionized flow. Depending on the type of cloud formation to dissipate, the working cells of the ionizer are tilted at a desired angle thus providing the required energy to the ascending air flow that induces said downflows. The influence depends on meteorological conditions and type of cloud formation. For example, frontal clouds (i.e. large cloud fields and Cumulus congestus clouds) should be dispersed in stages as shown in FIG. 9.

Figure 7:
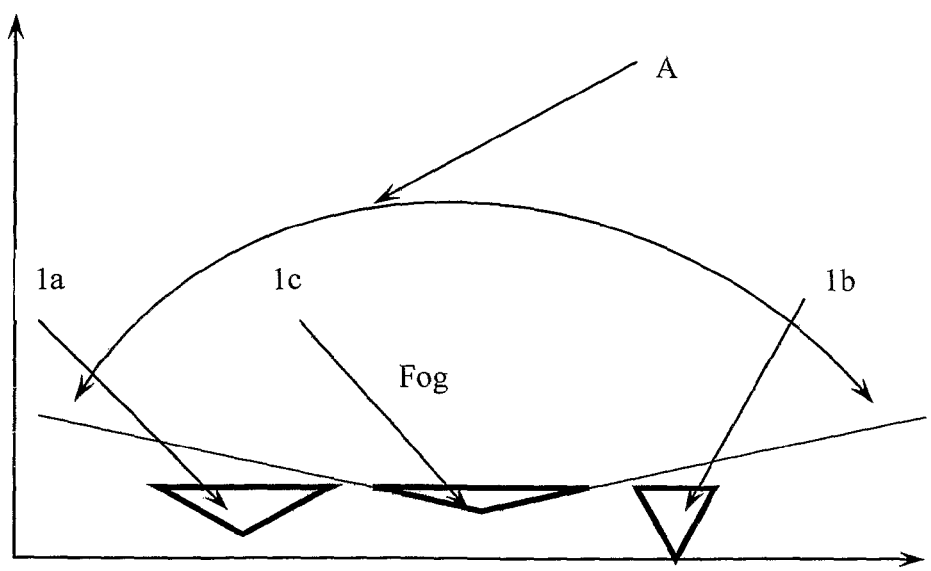
FIG. 7 also illustrates three ionizers/apparatuses 1a, 1b, 1c wherein the side surfaces are tilted at different angles. The figure shows the ionizer assembly 1c selected for dispersing fogs.

3. Dispersal of fog of any type is carried out by saturating it with active condensation nuclei consisting of negative ions. In this case the angle between the opposite working cells of the ionizer should be set at maximum, as shown in FIG. 7 (the apparatus/ionizer 1*c*). Said adjustment causes the ionized air flow being dissipated instead of being concentrated so as to increase the area being treated as much as possible. Negative ions attract weighted water droplets of fog and the condensation occurs with release of heat thus increasing the temperature of the surrounding air. As a result of condensation, some droplets become heavier and fall to the ground while the others do not manage to condense and thus evaporate due to the temperature rise. Thus, the fog is dissipated and a visibility range increases.

In all cases described herein, it may be useful to use more than one ionizer being similar to that described above. When using a group of ionizers, e.g. a group of three apparatuses, working cells of different ionizers can have different inclination angles while keeping the same angles within each one ionizer, depending on the purposes of treatment. Due to a variety of atmospheric conditions, it is not possible to provide versatile control over the weather with any of ionizers known in the prior art as configurations of said ionizers can not be changed operatively. As described above, the capability of changing the inclination angle of working cells of electrodes (under certain conditions) leads to not only expansion of the operating area of said ionizers but also qualitative change of the influence.

The invention is not limited to the disclosed embodiments. It can be also used for blowing the surface air within polluted areas as well for other cases of application of an inexpensive and ecologically clean local treatment of the atmosphere.

The invention claimed is:

1. An apparatus comprising an air ionizer, wherein: a shielding electrode, an emitting electrode and an extracting electrode are arranged in a parallel way; each electrode comprises coupled working cells formed by an electrical conductor that is arranged in a plane; all working cells of each electrode are tilted to the common center; each working cell of each electrode is mounted on a supporting frame in such a way that it is possible to adjust its inclination to an axis plane of the apparatus and to change its position relating to the other two opposite electrodes with their parallel orientation being unchanged; meanwhile the upper part of the extracting electrode and the upper part of the shielding electrode are located above the emitting electrode during operation.

2. The apparatus of claim 1, further comprising means for spraying water over said ionizer.

3. The apparatus of claim 1, comprising a stabilizing device to stabilize voltage at the emitting electrode.

4. The apparatus of claim 1, wherein the emitting electrode is further suitable for measuring current and voltage at the emitting electrode.

5. The apparatus of claim 2, comprising a stabilizing device to stabilize voltage at the emitting electrode.

6. The apparatus of claim 2, wherein the emitting electrode is further suitable for measuring current and voltage at the emitting electrode.

7. The apparatus of claim 3, wherein the emitting electrode is further suitable for measuring current and voltage at the emitting electrode.

8. The apparatus of claim 5, wherein the emitting electrode is further suitable for measuring current and voltage at the emitting electrode.

* * * * *